United States Patent [19]
Weinkauf et al.

[11] Patent Number: 6,036,963
[45] Date of Patent: Mar. 14, 2000

[54] GLUCONOLACTONES AND GLUCAROLACTONES AS ANTI-IRRITANTS IN COSMETIC COMPOSITIONS

[75] Inventors: Ronni Weinkauf, River Edge; Uma Santhanam, Tenafly; Laura Palanker, Jackson; Donald Rick, New Milford, all of N.J.; John Bartolone, Bridgeport, Conn.

[73] Assignee: Chesebrough-Ponds's USA Co., Division of Conopco, Inc., Greenwich, Conn.

[21] Appl. No.: 09/030,964

[22] Filed: Feb. 26, 1998

[51] Int. Cl.⁷ ..................................................... A61K 6/00
[52] U.S. Cl. ........................................... 424/401; 514/969
[58] Field of Search .............................. 424/401; 514/969

[56] References Cited

U.S. PATENT DOCUMENTS

| | | | |
|---|---|---|---|
| 4,363,815 | 12/1982 | Yu et al. | 424/274 |
| 5,091,171 | 2/1992 | Yu et al. | 424/642 |
| 5,385,938 | 1/1995 | Yu et al. | 514/557 |
| 5,554,654 | 9/1996 | Yu et al. | 514/557 |
| 5,654,340 | 8/1997 | Yu et al. | 514/574 |
| 5,665,776 | 9/1997 | Yu et al. | 514/557 |
| 5,677,340 | 10/1997 | Yu et al. | 514/557 |
| 5,703,122 | 12/1997 | Duffy | 514/474 |
| 5,716,625 | 2/1998 | Hahn et al. | 424/401 |

FOREIGN PATENT DOCUMENTS

| | | |
|---|---|---|
| 0 770 399 | 5/1997 | European Pat. Off. . |
| 0 852 946 | 7/1998 | European Pat. Off. . |
| 2 370 471 | 6/1978 | France . |

OTHER PUBLICATIONS

Berardesca, E et al. Alpha hydroxyacids modulate stratum corneum barrier function 1997 British Journal of Dermatology 137:934–938.

International Search Report in a corresponding application PC/EP 99/00764.

Derwent abstract of FR 2370471.

Patent Abstracts of Japan, JP 62 077312, Apr. 9, 1987.

Exuviance Sensitive Formula packaging, 1997.

Exuviance Essential Multi–Defense Day Creme SPF 15 packaging, 1997.

Exuviance Product Information Insert "Advanced Skin Care from the Discoverers of Alpha Hydroxyacid Technology."—4 pages, 1997.

*Primary Examiner*—Thurman K. Page
*Assistant Examiner*—Todd D. Ware
*Attorney, Agent, or Firm*—Rimma Mitelman

[57] ABSTRACT

Gluconolactone or glucarolactone in cosmetic skin care compositions, as anti-irritants, to reduce skin irritation, which may be intrinsic skin irritation or irritation caused by hydroxy acids or certain retinoids.

7 Claims, No Drawings

GLUCONOLACTONES AND GLUCAROLACTONES AS ANTI-IRRITANTS IN COSMETIC COMPOSITIONS

FIELD OF THE INVENTION

Gluconolactone or glucarolactone as an anti-irritant in cosmetic skin care methods and compositions.

BACKGROUND OF THE INVENTION

Some ingredients used in topical products are potentially irritating, especially to people with "sensitive skin."

As an example, hydroxy acids (HAs) and retinoids have been proven to deliver cosmetic benefits, such as improvement in the appearance of photodamaged or naturally aged skin, skin lightening, treatment of age spots, etc. Unfortunately, their use at high concentrations may occasionally be associated with skin irritation, e.g. skin redness and stinging sensation upon application. The irritation can be ameliorated by lowering the amount of an active ingredient in the composition or by reducing the active's penetration through the skin. A serious drawback of both approaches is that the efficacy is impaired. The HA related irritation can be reduced by raising the composition's pH but this method yields reduced efficacy due to a decreased HA penetration through the skin. It is desirable to reduce or eliminate the irritation potential of HAs and/or retinoids while maintaining their efficacy.

The occurrence, frequency and nature of irritation often varies from user to user. The severity of irritation to the susceptible user may range from mild to severe. Typical symptoms of irritation include itching (pruritus), stinging, burning, tingling, "tightness," erythema (redness) or edema (swelling).

Environmental conditions such as sunlight, wind, cold temperature and dry air, may cause or exacerbate the irritation. Additionally, soaps, detergents, cleansing products, shaving creams, alcohol and other products which remove some of the skin's protective lipids and/or secretions may increase the skin's permeability and sensitivity to topically-applied chemicals which would otherwise not produce irritation.

Similarly, the skin may become irritated due to infection, shaving abrasion, repeated or excessive washing or bathing, sun exposure, or other mechanical abrasion or injury.

In addition to chemical and environmental causes of skin irritation, many people have an inherent sensitivity or genetic predisposition to skin irritants ("intrinsic skin irritation"). Whatever the exact cause of irritation, many attempts have been made to reduce the irritation potential of topical products by identifying chemicals which tend to cause irritation and reducing their concentration or eliminating them from the products.

Unfortunately, it is often not feasible or practical to identify or eliminate all of the irritating chemical(s), particularly when the irritating chemical(s) are the active ingredient of the product or are required for formulation, preservative or other functional reasons.

The need exists, therefore, for a composition and method that prevents or reduces the skin irritation.

Van Scott et al. teach in numerous patents (e.g., U.S. Pat. No. 5,654,340; U.S. Pat. No. 5,677,340; U.S. Pat. No. 5,385,938 and U.S. Pat. No. 5,091,171) cosmetic compositions containing alpha-hydroxy acids, which may be present as lactones. Gluconolacone and glucarolactone (a.k.a. "saccharic acid lactone") are mentioned. Other lactones, however, which do not reduce irritation (see Example 1 below) are also mentioned. Van Scott et al. do not teach the use of any of the lactones for controlling or alleviating skin irritation A commercially available product line "Exuviance" includes several products with gluconolactone. For instance, Exuviance Fundamental Multiprotective Day Creme SPF 15—Sensitive Formula includes gluconolactone. The Exuviance product information insert describes gluconolactone as a poly hydroxyacid and teaches that poly hydroxyacids are more gentle to the skin than hydroxy acids. One of the Sensitive Formula products is described as a "soothing toning" formula. It is clear from the product information insert that gluconolactone is included in the formula as an anti-aging ingredient, as a less irritating alternative to a hydroxy acid. The product includes traditional soothing ingredients, e.g. aloe vera extract, further indicating that gluconolactone itself is not included as an anti-irritant. The insert does not teach the use of gluconolactone for treating skin that is already irritated.

Another Exuviance product, Exuviance Essential Multi-Defense Day Creme SPF 15, includes gluconolactone in combination with glycolic acid. Again, the product does not describe the use of gluconolactone for alleviating or controlling any skin irritation or skin irritation that may be caused by glycolic acid. Indeed, gluconolactone is used in the amount that appears insufficient to alleviate irritation.

In the Exuviance products, gluconolactone is included as an less irritating alternative to an anti-aging ingredient, a hydroxy acid. The Exuviance product does not employ gluconolactone as an anti-irritant and the product information insert does not teach that gluconolactone is an anti-irritant. By contrast, the present invention is based at least in part on the discovery that gluconolactone lowers the irritation of an already irritated skin and prevents irritation that may be caused by topical cosmetic product application.

Furthermore, prejudice exists against using gluconolactone as an anti-irritant, since gluconolactone is considered in the art as an irritating ingredient, albeit less irritating than a hydroxy acid. See for instance Hahn et al (U.S. Pat. No. 5,716,625) column 2, lines 44–59, which lists gluconolactone as a chemical which "may cause the skin to become more sensitive to irritation triggered by other topically-applied chemicals . . . " It is, therefore, surprising and unexpected that gluconolactone acts as an anti-irritant on an already irritated skin and was able to reduce irritation associated with the use of skin care cosmetic compositions.

SUMMARY OF THE INVENTION

The present invention includes, in part, a composition containing a cosmetic benefit ingredient selected from the group consisting of hydroxy acids and certain retinoids and further containing gluconolactone or glucarolactone as an anti-irritant.

The invention also provides a method for reducing skin irritation sensitivity (whether caused by the topical application of a composition containing HAs or retinoids or the skin that is intrinsically sensitive) the method comprising topically applying gluconolactone or glucarolactone. Thus, according to the inventive method, gluconolactone or glucarolactone may be co-present with HAs and/or retinoids in the same composition, or gluconolactone or glucarolactone may be applied from a separate composition.

According to the present invention, by virtue of topical application of gluconolactone or glucarolactone, the skin irritation is reduced or eliminated. It has been found as part of the present invention that not all known anti-irritants ameliorate HAs/retinoid induced irritation. Furthermore, it has been found that not all lactones are capable of being anti-irritants.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the composition, unless otherwise specified.

Gluconolactone or glucarolactone is an essential ingredient of the inventive methods and compositions.

The term "gluconolactone" includes the following structures:

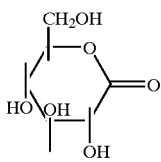

delta-gluconolactone

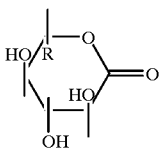

R=CH2OH
glucono-1,5-lactone

The term "glucarolactone" includes the following structures:

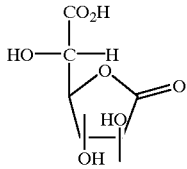

glucaro-3,6-lactone

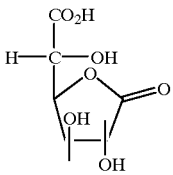

glucaro-1,4-lactone

The gluconolactone or glucarolactone is employed in an amount of at least 3%, preferably at least 4%, more preferably from 3% to 12%, most preferably from 4% to 12%, most preferably from 4% to 8%.

The inventive methods employ gluconolactone or glucarolactone, alone, or in combination with a potentially irritating ingredient, to reduce either the intrinsic skin irritation or the irritation caused by the ingredient.

The inventive compositions include either a hydroxy acid or a certain retinoid (not all retinoids are potentially irritating).

Hydroxyacids enhance proliferation and increase ceramide biosynthesis in keratinocytes, increase epidermal thickness, and increase desquamation of normal skin resulting in smoother, younger looking skin.

The hydroxy acid can be chosen from alpha-hydroxy acids, beta-hydroxyacids (e.g. salicylic acid), other hydroxycarboxylic acids (e.g., dihydroxycarboxylic acid, hydroxydicarboxylic, hydroxytricarboxylic) and mixtures thereof or combination of their stereoisomers (DL, D or L).

Preferably the hydroxy acid is chosen from alpha-hydroxy acids having the general structure (1)

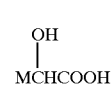

(1)

where M is H or a saturated or an unsaturated, straight or branched hydrocarbon chain containing from 1 to 27 carbon atoms.

Even more preferably the hydroxy acid is chosen from lactic acid, 2-hydroxyoctanoic acid, hydroxylauric acid, glycolic acid, and mixtures thereof. When stereo isomers exist, L-isomer is most preferred.

It is to be understood that depending on the pH of the composition, the hydroxy acid may be present as a salt, e.g. ammonium or potassium or sodium salt.

Although the inventive compositions may have any pH in the general range of 2.5 to 10, the inventive compositions are particularly useful when they are at an acidic pH (especially if they contain a hydroxy acid), preferably 3–5 and most preferably at a pH of 3–4, because such compositions are particularly irritating.

Retinoids enhance keratinocyte proliferation in vitro, increase epidermal thickness and increase collagen synthesis by dermal fibroblasts. This results in protection from sun damage and smoothing of wrinkled skin. The term "retinoids" as used herein includes retinoic acid, retinol, retinal and $C_2$–$C_5$ retinyl esters. Included in the term "retinoic acid" are 13-cis retinoic acid and all-trans retinoic acid.

The term "retinol" includes the following isomers of retinal: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_2$–$C_5$ esters of retinol, preferably C2 and $C_3$ esters, and most preferably $C_2$ ester because it is more commonly available. Retinyl esters included in the invention are also known as: retinyl acetate, retinyl propionate, retinyl butyrate, and retinyl pentanolate.

A particular advantage of the inventive compositions is that higher amounts of hydroxy acids or retinoids may be employed without causing skin irritation. Preferably the amount of the hydroxy acid component present in the composition according to the invention is from 0.01 to 20%, more preferably from 2 to 12% and most preferably from 4 to 12% by weight.

A retinoid may be present in the inventive compositions in an amount 33 to 330,000 IU per gram of the composition, preferably 330 to 16,500 IU, most preferably 1,650 to 6,600 IU. Again, a higher amount of a retinoid may be employed in the inventive compositions without causing skin irritation, due to the co-presence of gluconolactone or glucarolactone.

Most preferred inventive compositions containing gluconolactone or glucarolactone anti-irritant include retinol and/or glycolic acid and/or lactic acid because these ingredients have been found to cause irritation yet they were found to be particularly efficacious at delivering cosmetic benefits.

The compositions and methods according to the invention also comprise a cosmetically acceptable vehicle to act as a diluent, dispersant or carrier for the active ingredients in the composition, so as to facilitate their distribution when the composition is applied to the skin.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition. The amount of vehicle may range from about 2 to about 99 wt %, preferably from about 50 to about 99%, most preferably from about 80 to 99%, by weight of the total composition.

According to the present invention, the vehicle is preferably at least 60 wt. % water, by weight of the vehicle. The inventive compositions are preferably oil-water emulsions, in order to improve dermal delivery of hydroxy acids (See Sah A., "An in-vitro study of the effect of formulation variables and product structure on the delivery of alpha-hydroxy acid (Lactic acid) to skin", MS Thesis, Department of Pharmaceutical Sciences of the College of Pharmacy, University of Cincinnati, Ohio, July 1996). Such improved delivery is frequently accompanied by increased irritation/sting, making the use of gluconolactone or glucarolactone in such emulsions particularly critical. In the preferred oil-in-water emulsions according to the present invention, water comprises at least 50 wt. % of the inventive emulsion, most preferably from 50 to 70 wt. %, by weight of the composition.

Optional Skin Benefit Materials and Cosmetic Adjuncts

Various types of active ingredients may be present in cosmetic compositions of the present invention. Actives are defined as skin benefit agents other than emollients and other than ingredients that merely improve the physical characteristics of the composition. Although not limited to this category, general examples include anti-wrinkle compounds and sunscreens and tanning agents.

Sunscreens include those materials commonly employed to block ultraviolet light. Illustrative compounds are titanium dioxide, the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other component materials may range anywhere from 0.001% up to 20% by weight of the composition.

Use of the Composition

The composition according to the invention is intended primarily as a product for topical application to human skin, especially as an agent for conditioning and smoothening the skin, and preventing or reducing the appearance of wrinkled, aged and/or photodamaged skin.

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

According to the present inventive method, the skin irritation, either intrinsic or induced by the active ingredient, is reduced or eliminated by topical application of gluconolactone or glucarolactone. Gluconolactone or glucarolactone may be co-present with the active, or it may be applied to the skin separately from the active.

The following specific examples further illustrate the invention, but the invention is not limited thereto.

EXAMPLE 1

The antiinflammatory potential of the test compounds was assessed by the ability of the compound to inhibit IL-1 alpha-induced PGE2. IL-1 alpha and PGE2 are well known mediators of inflammation in the skin. See Greaves et al., "Prostaglandins, leukotrienes, phospholipase, platelet activating factor and cytokines: an integrated approach to inflammation of human skin," Arch. Dermatol. Res. (1988) 280 (Supp):S33–S41

Neonatal human dermal fibroblasts (passage 5–9) were seeded at a density of 7500 cells per well in 96-well tissue culture treated plates (Corning-Costar, Corning, N.Y.). The medium used was Dulbecco's Modified Eagle's Medium (DMEM), high-glucose (Gibco/Life Technologies, Gaithersburg, Md.) supplemented with 2 mM L-glutamine, 10% fetal bovine serum, and antibiotic and anti mycotic solutions (all also Life Technologies). After 48 hours, each well was rinsed twice with 200 microlliters serum-free DMEM and the cells dosed with 200 microlliters in DMEM+L-glutamine containing IL-1alpha at 1 ng/ml and/or active. After six hours, cells were examined microscopically for qualitative viability, and the medium was harvested and frozen until analysis. Each treatment was run in quadruplicate.

Enzyme immunoassay was performed using a commercial PGE2 kit (Amersham, Buckinghamshire, England). PGE2-specific antibody is precoated on a set of microtiter wells. The assay is based on the competition between unlabelled PGE2 (standard or sample) and a fixed quantity of peroxidase labelled PGE2 for a limited amount of the well-bound PGE2-specific antibody. Standards of 0, 1, 2, 4, 8, 16, and 32 pg/well or 50 ml media/well were applied with 50 microlliters /well of 0.1 M phosphate buffer pH 7.5 for 3 hours at 4° C. At the end of this incubation, 50 microlliters/well of horseradish peroxidase-conjugated PGE2 was added to all wells and the plate incubated for 1 hour at 4° C. Plates were washed 4 times with 300 microlliters/well 0.01 M phosphate buffer pH 7.5 containing 0.5% Tween 20. 150 microlliters/well 3,3',5,5'-tetramethylbenzidine/hydrogen peroxide substrate in 20% dimethylformamide was added and the plate incubated exactly 30 minutes at room temperature. Reaction was stopped by adding 100 microlliters/well 1 M sulfuric acid. The Dynatech MR7000 microplate spectrophotometer (Dynatech, Chantilly, Va.) was used to quantitate color in the wells by reading absorbance at 450 nm. A standard curve was plotted and the amount of PGE2 in the samples was extrapolated from the curve.

The antiinflammatory potential of the test compounds was assessed by the ability of the compound to inhibit IL-1 alpha-induced PGE2 and was expressed as the ratio (A/B) of PGE2 produced by the cells treated with the test compound+IL-1 alpha (A) to that by the cells treated with IL-1 alpha alone (B). Statistical significance was determined using the student's t-test. Compounds listed in Tables 1 and 2 were tested using the in vitro PGE2 method. A/B value of less than 1 indicated that the test compound inhibited the release of PGE2 by IL-1alpha and had anti-inflammatory potential, if statistically significant.

TABLE 1

| EFFECTIVE | | | |
|---|---|---|---|
| treatment | concentration | A/B | p value (A vs. B) |
| glucaro-1,4-lactone | 0.5 mM | 0.6[a] | .020 |
| glucaro-1,4-lactone | 5 mM | 1.1 | .74 |
| glucaro-3,6-lactone | 0.5 mM | 0.6[a] | .026 |
| glucaro-3,6-lactone | 5 mM | 0.9 | .71 |
| d-gluconolactone | 0.5 mM | 1.0 | .84 |
| d-gluconolactone | 5 mM | 0.5[a] | .0026 |
| glucono-1,5-lactone | 0.5 mM | 0.5[a] | .0026 |
| glucono-1,5-lactone | 5 mM | 0.6[a] | .0011 |

[a]significant decrease in PGE2 production

TABLE 2

| INEFFECTIVE | | | |
|---|---|---|---|
| treatment | concentration | A/B | p value (A vs. B) |
| galactonic acid | 0.5 | 1.1 | .40 |
| galactonic acid | 0.05 | 0.8 | .45 |
| D-galactonolactone | 5 | 2.1 | .041 |
| D-galactonolactone | 0.5 | 1.6 | .12 |
| L-galactonolactone | 5 | 2.3 | .027 |
| L-galactonolactone | 0.5 | 2.4 | .021 |
| glucaric acid | 0.05 mM | 0.9 | .94 |
| glucaric acid | 0.5 mM | 1.8 | .14 |
| gluconic acid | 0.5 | 0.8 | .51 |
| gluconic acid | 5 mM | 0.9 | .77 |
| glucuronic acid | 0.5 | 1.0 | .79 |
| glucuronic acid | 0.05 | 1.4 | .17 |

TABLE 2-continued

| INEFFECTIVE | | | |
|---|---|---|---|
| treatment | concentration | A/B | p value (A vs. B) |
| glucuronolactone | 0.5 | 1.7 | 0.071 |
| glucuronolactone | 0.05 | 1.8 | .075 |
| D-gulonolactone | 0.5 | 0.9 | .71 |
| D-gulonolactone | 0.05 | 0.7 | .057 |
| L-gulonolactone | 0.5 | 1.4 | .094 |
| L-gulonolactone | 0.05 | 1.1 | .59 |
| ribonic acid | 5 | 3.0 | .0064 |
| ribonic acid | 0.5 | 2.6 | .011 |
| ribonolactone | 5 | 2.5 | .025 |
| ribonolactone | 0.5 | 2.6 | .011 |

It can be seen from the results in Table 1, that glucaro-1,4-lactone, glucaro-3.6-lactone, delta-gluconolactone, and glucono-1,5-lactone significantly reduced IL-1 alpha-induced PGE2 production in vitro.

It can be seen from the results in Table 2, that not all lactone compounds were effective in significantly reducing IL-1 alpha induced PGE2 production in vitro.

EXAMPLE 2

Irritation Test Method

Four Exposure Patch Test: The objective was to compare the level of irritation produced by various test materials after repeated patch applications. The test materials were held in contact with the skin under occlusive conditions. The outer upper arm of the panelist was designated as thea rea of application. Bandage type dressing (Scanpor tape) was used to hold the patches (25 mm Hill Top Chamber fitted with 18 mm diameter disc of Webril padding) into place. Both upper arms of the panelist were used. Patches were applied in a balanced random order.

Patches were applied at 9:00 o'clock Monday morning and removed at 9:00 o'clock Tuesday morning (24 hour exposure). A new set of patches was applied at 3:00 o'clock Tuesday afternoon and removed Wednesday morning at 9:00 o'clock (18 hour exposure). A third set of patches was applied at 3:00 o'clock Wednesday afternoon and removed Thursday morning at 9:00 o'clock (18 hour exposure). A final set of patches was applied at 3:00 o'clock Thursday afternoon and removed Friday morning at 9:00 o'clock (18 hour exposure).

Each time the patches were removed, the sites were rinsed with warm water and patted dry. The test sites were then marked with a surgical skin marking pen to ensure location for grading and subsequent patch applications. Test sites were evaluated at 3:00 p.m. on Tuesday, Wednesday, Thursday, and Friday of the study, prior to re-patching.

Skin irritation such as moderate redness, dryness, and/or itching of the test site is expected. Swelling of the test sites was possible. If any test site had moderate redness or any swelling at any evaluation, that particular test site was not repatched.

The test sites on each arm were visually ranked by two trained examiner under consitent lighting. The test sites were ranked in order of severity. The examiner ranking responses at the first evaluation period continued ranking the sites each day throughout the study.

In ranking the reactions, the site with the most sever response was given the lowest score. The site with the second most severe response was given the second lowest score, etc. There was no forced ranking. If two or more sites had no response or the same response (no difference between sites), an average of the ranks was assigned. If a site had been discontinued, due to degree of irritation, the site retained the rank it received at the time dosing was discontinued.

Statistical Analysis

The ranking results from the patch treatments were statistically compared by nonparametric statistical methods. The test materials containing the anti-irritants were compared to the corresponding control containing only hydroxy acid and/or retinoid, using Friedman's Rank Sum at each evaluation point with the panelist acting as a block (i.e., each panelist was tested with each test treatment). A p-value of <0.10 was considered statistically significant.

Compositions containing ingredients as indicated in Tables 3a, 3b, and 3c, were tested using the Irritation Test Method. 17 subjects were tested for Table 3a, 19 for Table 3b, and 20 for Table 3c. The results that were obtained are summarized in Table 3. The higher the sum of ranks, the less is the irritation.

EMULSION BASE FORMULA

| FULL CHEMICAL NAME OR CFTA NAME | TRADE NAME AND % ACTIVE | WT. % |
| --- | --- | --- |
| water, DI | | 46.54 |
| disodium EDTA | Sequesterene Na2 | 0.05 |
| magnesium aluminum silicate | Veegum Ultra | 0.6 |
| methyl paraben | Methyl Paraben | 0.15 |
| simethicone | DC Antifoam Emulsion | 0.01 |
| butylene glycol 1,3 | Butylene Glycol 1,3 | 3.0 |
| hydroxyethylcellulose | Natrosol 25OHHR | 0.5 |
| glycerine, USP | Glycerine USP | 2.0 |
| xanthan gum | Keltrol 1000 | 0.2 |
| triethanolamine | Triethanolamine 99 (%) | 1.2 |
| stearic acid | Pristerene 4911 | 3.0 |
| propyl paraben NF | Propylparaben NF | 0.1 |
| glyceryl hydrostearate | Naturechem GMHS | 1.5 |
| stearyl alcohol | Lanette 18DEO | 1.5 |
| isostearyl palmitate | Protachem ISP | 6.0 |
| C12–15 alcohols octanoate | Hetester FAO | 3.0 |
| dimethicone | Silicone Fluid 200 (50 cts) | 1.0 |
| cholesterol NF | Cholesterol NF | 0.5 |
| sorbitan stearate | Sorbitan Stearate | 1.0 |
| butylated hydroxytoluene | Embanox BHT | 0.05 |
| tocopheryl acetate | Vitamin E Acetate | 0.1 |
| PEG-100 stearate | MYRJ 59 | 2.0 |
| sodium stearoyl lactylate | Pationic SSL | 0.5 |
| retinyl palmitate | Vit. A Palmitate 84% | 0.06 |
| hydroxy caprylic acid | Hydroxy caprylic acid | 0.1 |
| water, DI | | q.s. to 99.80 |
| alpha-bisabolol | Alpha-bisabolol | 0.2 |
| pH | | 7–8 |

Additional ingredients in the Examples below were added in place of water. pH was adjusted with ammonium hydroxide or hydrochloric acid. Glycolic acid was 70% active, as received.

TABLE 3a

Irritation Test Results

| COMPOSITION | INGREDIENTS | IRRITATION SCORE (Day 4) |
| --- | --- | --- |
| 1 | Base Formula | 58.5 |
| 2 | Base Formula + 8% Glycolic acid, pH 3.8 | 52.5 |
| 3 | Composition #2 + 4% Gluconolactone, pH 3.8 | 71.0[a] |

[a]significantly less irritating than composition 2.

TABLE 3b

Irritation Test Results

| COMPOSITION | INGREDIENTS | IRRITATION SCORE (Day 4) |
| --- | --- | --- |
| 1 | Base Formula | 83.0 |
| 2 | Base Formula + 8% Glycolic acid, pH 3.8 | 66.5 |
| 4 | Composition #2 + 1% Gluconolactone, pH 3.8 | 72.0[b] |

[b]not significantly less irritating than composition 2.

TABLE 3c

Irritation Test Results

| COMPOSITION | INGREDIENTS | IRRITATION SCORE (Day 4) |
| --- | --- | --- |
| 1 | Base Formula | 79.5 |
| 2 | Base Formula + 8% Glycolic acid, pH 3.8 | 72.0 |
| 5 | Composition #2 + 2% Gluconolactone, pH 3.8 | 74.0[b] |

[b]not significantly less irritating than composition 2.

It can be seen from the results in Table 3a that 4% gluconolactone (Composition 3) significantly reduced the irritation induced by composition #2 (containing 8% glycolic acid) whereas inclusion of 1% or 2% gluconolactone (compositions 4 and 5 in Tables 3b and 3c) did not significantly affect irritation induced by 8% glycolic acid.

EXAMPLE 3

Compositions containing ingredients as indicated in Table 4, were tested using the Irritation Test Method. 20 subjects were tested. The results that were obtained are summarized in Table 4. The higher the sum of ranks, the less is the irritation.

TABLE 4

Irritation Test Results

| COMPOSITION | INGREDIENTS | IRRITATION SCORE (Day 4) |
| --- | --- | --- |
| 1 | Base Formula | 68.5[a] |
| 2 | Base Formula (Composition #1) + 8% Glycolic acid, pH 3.8 | 57 |
| 6 | Base Formula (Composition #1) + 8% Gluconolactone | 100.5[b] |

[a]significantly less irritating than composition 2 (Day 2)
[b]significantly less irritating than composition 1 and 2

It can be seen from the results in Table 4, that gluconolactone (composition #6) significantly reduced the irritation of the Base Formula which does not contain glycolic acid. This Example demonstrates that the inventive method is useful for reducing skin irritation even in the absence of potentially irritating hydroxy acid or retinoid.

COMPARATIVE EXAMPLE 4

Compositions 1, 5 and 11–14 containing ingredients as indicated in Table 5 were tested using the Irritation Test Method described in Example 2. Seventeen subjects were tested. The results that were obtained are summarized in Table 5. The lower the sum of ranks, the greater is the irritation

TABLE 5

Irritation Test Results

| COMPOSITION # | INGREDIENTS | SUM OF RANKS (DAY 4) |
|---|---|---|
| 1 | Base Formula | 74.5[a] |
| 7 | Base Formula + 8% Glycolic + 0.075% Retinol | 61.5 |
| 8 | Composition #7 + 1% Green Tea | 51.0 |
| 9 | Composition #7 + 0.1% K2 Glycyrrohetinic Acid | 54.5 |
| 10 | Composition #7 + 3% Quench T* | 58.5 |
| 11 | Composition #7 + 3% Polyol Prepolymer -2** | 57.0 |

[a]Statistically less irritating than composition #7
*An anti-irritant from Centerchem (containing water, butylene glycol, kola bean extract, guarana extract, and mate extract).
**An anti-irritant from Penederm, Inc. (CFTA name PPG-12/SMDI).

It can be seen from the results in Table 5 that none of the known anti-irritants tested were able to significantly reduce the irritation induced by composition #5 (containing 8% Glycolic Acid and 0.075% Retinol).

Examples 5–11 illustrate topical compositions according to the present invention. The compositions can be processed in conventional manner. They are suitable for cosmetic use. In particular the compositions are suitable for application to wrinkled, rough, dry, flaky, aged and/or UV-damaged skin to improve the appearance and the feel thereof as well as for application to healthy skin to prevent or retard deterioration thereof.

EXAMPLE 5

A typical oil-in-water emulsion within the scope of the invention is as follows:

| chemical name | wt. % |
|---|---|
| propylene glycol | 1 |
| glycerin | 1 |
| hydroxyethylcellulose | 0.5 |
| magnesium aluminum silicate | 0.5 |
| imidazolidinyl urea | 0.5 |
| tetrasodium EDTA | 0.05 |
| petrolatum | 2 |
| isopropyl palmitate | 5 |
| dimethicone | 0.5 |
| cholesterol | 0.5 |
| cetyl alcohol | 0.5 |
| isostearic acid | 3 |
| retinyl palmitate | 0.1 |
| peg-40 stearate | 1 |
| peg-100 stearate | 1 |
| sorbitan stearate | 1 |
| delta-gluconolactone | 4 |
| glycolic acid | 7 |
| ammonium hydroxide | to pH 4.0 |
| water DI | qs to 100% |

EXAMPLE 6

Another typical oil-in-water emulsion within the scope of the invention is as follows:

| chemical name | wt. % |
|---|---|
| propylene glycol | 1 |
| hydroxyethylcellulose | 0.5 |
| magnesium aluminum silicate | 0.5 |
| imidazolidinyl urea | 0.2 |
| petrolatum | 2 |
| isopropyl palmitate | 5 |
| dimethicone | 0.5 |
| cholesterol | 0.5 |
| stearic acid | 3 |
| isostearic acid | 1.5 |
| glycerol stearate | 1.5 |
| peg-40 stearate | 1 |
| peg-100 stearate | 1 |
| sorbitan stearate | 1 |
| cetyl alcohol | 0.5 |
| glucaro-3,6-lactone | 5 |
| glycolic acid | 10 |
| ammonium hydroxide | to pH 3.8 |
| water DI | qs to 100% |

EXAMPLE 7

A typical water-in-oil dispersion within the scope of the invention is as follows:

| chemical name | wt. % |
|---|---|
| isostearyl neopentanoate | 20 |
| peg-8 caprylic/capric glycerides | 6 |
| cetyl octanoate | 17 |
| polyglyceryl-6 dioleate | 15 |
| cyclomethicone | 20 |
| glyceryl isostearate | 0.5 |
| isostearic acid | 0.5 |
| ceramide III | 0.1 |
| ppg-5-cetheth-20 | 3 |
| L-lactic acid/potassium lactate | 6 |
| hydroxycaprylic acid | 0.1 |
| water DI | 1.3 |
| glucaro-1,4-lactone | 10 |

EXAMPLE 8

The following oil-in-water emulsion within the scope of the invention is prepared:

| chemical name | wt. % |
|---|---|
| glycerin | 1 |
| tetrasodium EDTA | 0.1 |
| cetyl alcohol | 1 |
| stearyl alcohol | 1 |
| mineral oil | 5 |
| dimethicone | 1 |
| cyclomethicone | 0.5 |
| dimethiconol | 0.2 |
| polyquaternium-37 | 2 |
| steareth-21 | 1 |
| steareth-2 | 0.5 |
| salicylic acid | 2 |
| delta-gluconolactone | 4 |
| triethanolamine to pH | 3.0 |
| water DI | qs to 100% |

EXAMPLE 9

The following oil-in-water emulsion within the scope of the invention is prepared:

| chemical name | wt. % |
| --- | --- |
| xanthan gum | 0.2 |
| disodium EDTA | 0.1 |
| sodium PCA | 0.5 |
| diazodinyl urea | 0.3 |
| titanium dioxide | 1 |
| stearic acid | 3 |
| cyclomethicone | 0.3 |
| cetyl alcohol | 0.5 |
| glyceryl stearate | 0.5 |
| peg-100 stearate | 0.5 |
| steareth-2 | 0.2 |
| lecithin | 0.5 |
| tocopherol | 0.2 |
| octyl methoxycinnamate | 6 |
| glucono-1,5-lactone | 6 |
| glycolic acid | 3 |
| malic acid | 2 |
| lactic acid | 2 |
| green tea extract | 1 |
| triethanolamine | to pH 3.8 |
| water DI | qs to 100% |

EXAMPLE 10

The following oil-in-water emulsion within the scope of the invention is prepared:

| chemical name | wt. % |
| --- | --- |
| all-trans retinoic acid | 0.05 |
| light mineral oil | 10 |
| stearoxytrimethylsilane and stearyl alcohol | 5 |
| dimethicone | 2 |
| stearyl stearate | 10 |
| quaternium-15 | 3 |
| peg-22 dodecyl glycol copolymer | 1 |
| glucaro-3,6-lactone | 3 |
| sorbitol | 0.5 |
| methyl paraben | 0.2 |
| disodium EDTA | 0.1 |
| butylated hydroxytoluene | 0.1 |
| water DI | qs to 100% |

EXAMPLE 11

The following oil-in-water emulsion within the scope of the invention is prepared:

| chemical name | wt. % |
| --- | --- |
| squalane | 20 |
| macadamia oil | 5 |
| pentaerythritol tetraoctanoate | 15 |

-continued

| chemical name | wt. % |
| --- | --- |
| petrolatum | 5 |
| glyceryl stearate | 3 |
| tocopherol acetate | 0.5 |
| butylated hydroxytoluene | 0.05 |
| methyl paraben | 0.15 |
| propyl paraben | 0.15 |
| retinol | 0.1 |
| glucaro-1,4-lactone | 5 |
| sodium citrate | 1 |
| ascorbic acid | 1 |
| butylene glycol | 2 |
| glycerol | 2 |
| bentone clay | 0.2 |
| disodium EDTA | 0.05 |
| water DI | qs to 100% |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic skin care composition comprising:

(i) a compound selected from the group consisting of retinol, retinoic acid, retinal, $C_2$–$C_5$ retinyl ester and mixtures thereof;

(ii) gluconolactone or glucarolactone in an amount of from about 3% to about 12%; and (iii) cosmetically acceptable vehicle.

2. The composition of claim 1, wherein the composition is an oil-in-water emulsion.

3. The composition of claim 1, wherein the pH of the composition is in the range of from 3 to 5.

4. An oil-in-water cosmetic skin care emulsion composition comprising:

(i) a hydroxy acid;

(ii) gluconolactone or glucarolactone in an amount of from about 3% to about 12%; and (iii) cosmetically acceptable vehicle.

5. The composition of claim 4, wherein the pH of the composition is in the range of from 3 to 5.

6. The composition of claim 4 wherein the hydroxy acid is present in an amount of from about 0.01% to about 20%.

7. The composition of claim 4 wherein the amount of the hydroxy acid is from about 2% to about 12%.

* * * * *